United States Patent [19]
Burkhead et al.

[11] Patent Number: 5,385,536
[45] Date of Patent: Jan. 31, 1995

[54] ORTHOPEDIC BRACE FOR ARM AND SHOULDER

[75] Inventors: Wayne Z. Burkhead, 2909 Lemmon Ave., Dallas, Tex. 75204; Bernard E. McConnell; Thomas E. McConnell, both of Greenville, Tex.

[73] Assignee: Wayne Z. Burkhead, Dallas, Tex.

[21] Appl. No.: 22,689

[22] Filed: Mar. 1, 1993

[51] Int. Cl.6 ............................................. A61F 5/00
[52] U.S. Cl. ........................................ 602/20; 602/5; 2/45
[58] Field of Search ............... 602/4, 5, 20; 2/44, 2/45; 128/25 R, 26, 870, 874, 875

[56] References Cited

U.S. PATENT DOCUMENTS

| | | | |
|---|---|---|---|
| 1,340,630 | 5/1920 | Maddox | 602/20 |
| 3,780,729 | 12/1973 | Garnett | 128/94 |
| 3,952,733 | 4/1976 | Williams | 128/94 |
| 4,180,870 | 1/1980 | Radulovic et al. | 3/1.2 |
| 4,241,731 | 12/1980 | Pauley | 128/94 |
| 4,373,517 | 2/1983 | Criscuolo | 128/75 |
| 4,417,569 | 11/1983 | Brudny | 128/77 |
| 4,480,637 | 11/1984 | Florek | 128/94 |
| 4,497,316 | 2/1985 | Lilla | 128/94 |
| 4,651,719 | 3/1987 | Funk et al. | 128/25 R |
| 4,708,510 | 11/1987 | McConnell et al. | 403/90 |
| 4,807,609 | 2/1989 | Meals | 128/87 |
| 4,836,195 | 6/1989 | Berrehail | 128/83 |
| 4,878,490 | 11/1989 | Scott | 128/77 |
| 4,896,660 | 1/1990 | Scott | 128/77 |
| 5,000,168 | 3/1991 | Lipson | 602/20 |

*Primary Examiner*—Richard J. Apley
*Assistant Examiner*—Beverly A. Meindl
*Attorney, Agent, or Firm*—Dennis T. Griggs

[57] ABSTRACT

An orthopedic brace for rigidly supporting a human arm and shoulder, having a positioning rod for infinitely varying the elevation of the arm through a coarse adjustment and a fine adjustment, and having universal joints on the positioning rod for infinitely varying the orientation of the arm.

6 Claims, 5 Drawing Sheets

ORTHOPEDIC BRACE FOR ARM AND SHOULDER

FIELD OF THE INVENTION

This invention is generally related to orthopedic devices for immobilizing and supporting limbs of patients who are undergoing surgical or other medical treatment of their limbs or who have suffered injury to their limbs.

BACKGROUND OF THE INVENTION

It often happens that an important part of the medical treatment of an arm or shoulder injury consists of the rigid immobilization and support of the arm of the injured person, usually accomplished by means of an orthopedic brace. Such injuries typically involve bone fractures and strain, tearing or rupture of one or more connective ligaments. After reduction of the fracture and repair of ligaments, the injury is treated by holding the shoulder in a neutral position and immobilizing the arm in a rigid cast. The rigid cast, which is typically molded plastic or resin, is replaced from time to time over a period of several weeks as swelling is reduced. Such rigid casts are heavy, limit the mobility of the patient, and may cause joint stiffening and muscle atrophy. It will be appreciated that because of the rigid nature of the molded cast, wound treatment procedures, bathing and skin treatments must be postponed until the cast is removed.

Such treatment may be required in order to allow healing of the arm or shoulder after surgery, or simply to allow natural healing by removing stress from the injured limb. Healing may occur through the recession of inflammation, for instance, or through the regeneration of bone or muscle tissues after a broken bone is set or after surgical correction of a physical disfunction. Examples of such disfunction are traumatized or arthritic joints or traumatized soft tissues.

The range of such dysfunctions and of the required treatments obviously varies greatly, and each different treatment may require a different type of immobilization and support of the limb. Shoulder injuries may require that the arm be supported in a lower posture, while arm injuries may require that the arm be supported in a more elevated posture. Similarly, the healing process may be optimized if the arm is angled more toward the front of the patient's body, while in another type of injury or for a different patient, angling the arm more toward the rear may be optimal. Still further, the physician may prefer to position the hand lower than the elbow in some cases and higher than the elbow in other cases. It may also be desirable to position the elbow at an angle either greater or less than a right angle. It is also often necessary to adjust an orthopedic brace during use, and it is obviously desirable to be able to reconfigure a brace for use by a different patient.

OBJECTS OF THE INVENTION

It will be appreciated that a brace used to immobilize and support a limb, specifically an arm, should ideally be adjustable so as to allow the attending physician to select the optimum elevation and orientation of the patient's arm. Such selection should cover the full range of possible angles and elevations at which the patient's arm may be positioned, both for the upper arm and for the forearm. Ideally, the selection over this full range should be variable and not limited to a few selectable positions. Moreover, the angle over which this variation may range should not be limited to a two dimensional angle, such as in simply raising and lowering the arm at the patient's side. It should instead involve a range of angles in three dimensions, or compound angles. For instance, the upper arm should be supportable at any angle up or down, and at any angle forward or rearward, from a nominal reference direction straight out to the patient's side. Similarly, the forearm should be supportable through a full range of compound angles relative to the upper arm. The variable adjustment should be possible while the brace is being worn by the patient, and the brace should be capable of being rigidly locked in each desired position.

SUMMARY OF THE INVENTION

The present invention is an orthopedic brace having a harness for attachment of the brace to a patient, a support for the upper arm and the forearm, and a positioning assembly which is capable of positioning the arm support at any desired elevation relative to the harness and at any desired orientation. The positioning assembly can typically raise or lower the elevation of the arm support by one or both of two methods. First, the positioning assembly can be mounted at different elevations on the harness. Second, the positioning assembly can be extended or retracted in length. Assisting in this variation of the elevation of the arm support and enabling the variation of the orientation of the arm support are two universal joints. Each of the universal joints is located at an end of the positioning assembly next to either the harness or the arm support, and each universal joint may be locked rigidly at any compound angle desired. The apparatus of the present invention can also be configured to support either the right arm or the left arm of a patient.

According to one aspect of the invention, a telescoping rod is included in the positioning assembly, and the universal joints are ball and socket joints.

The construction and function of the present invention will be understood by one skilled in the art after reading the following description with reference to the attached drawings.

DETAILED DESCRIPTION OF THE PREFERRED EMBODIMENT

Figure 1:
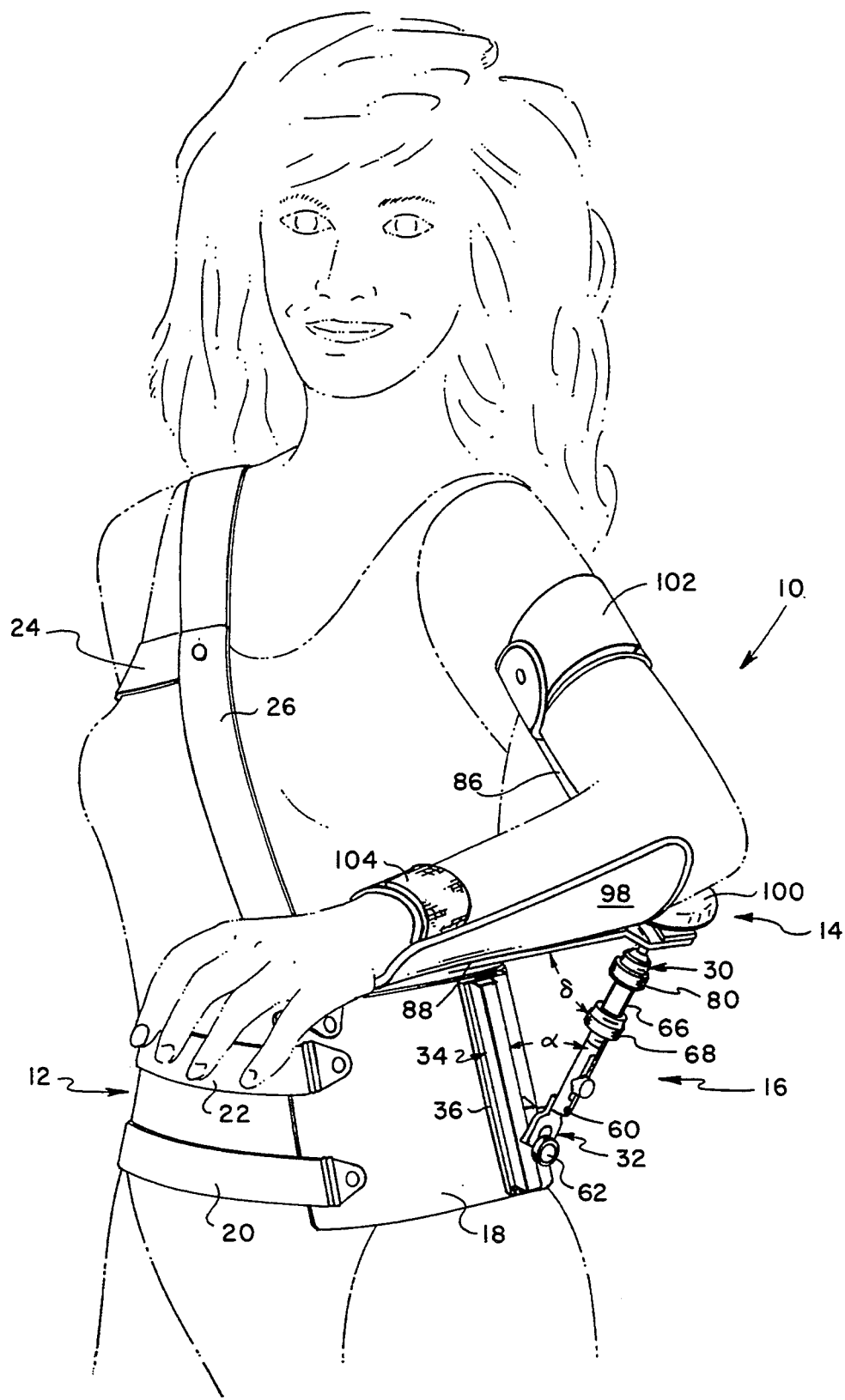
FIG. 1 is a front perspective view of the orthopedic brace of the present invention for supporting the left arm of a patient.
Figure 2:
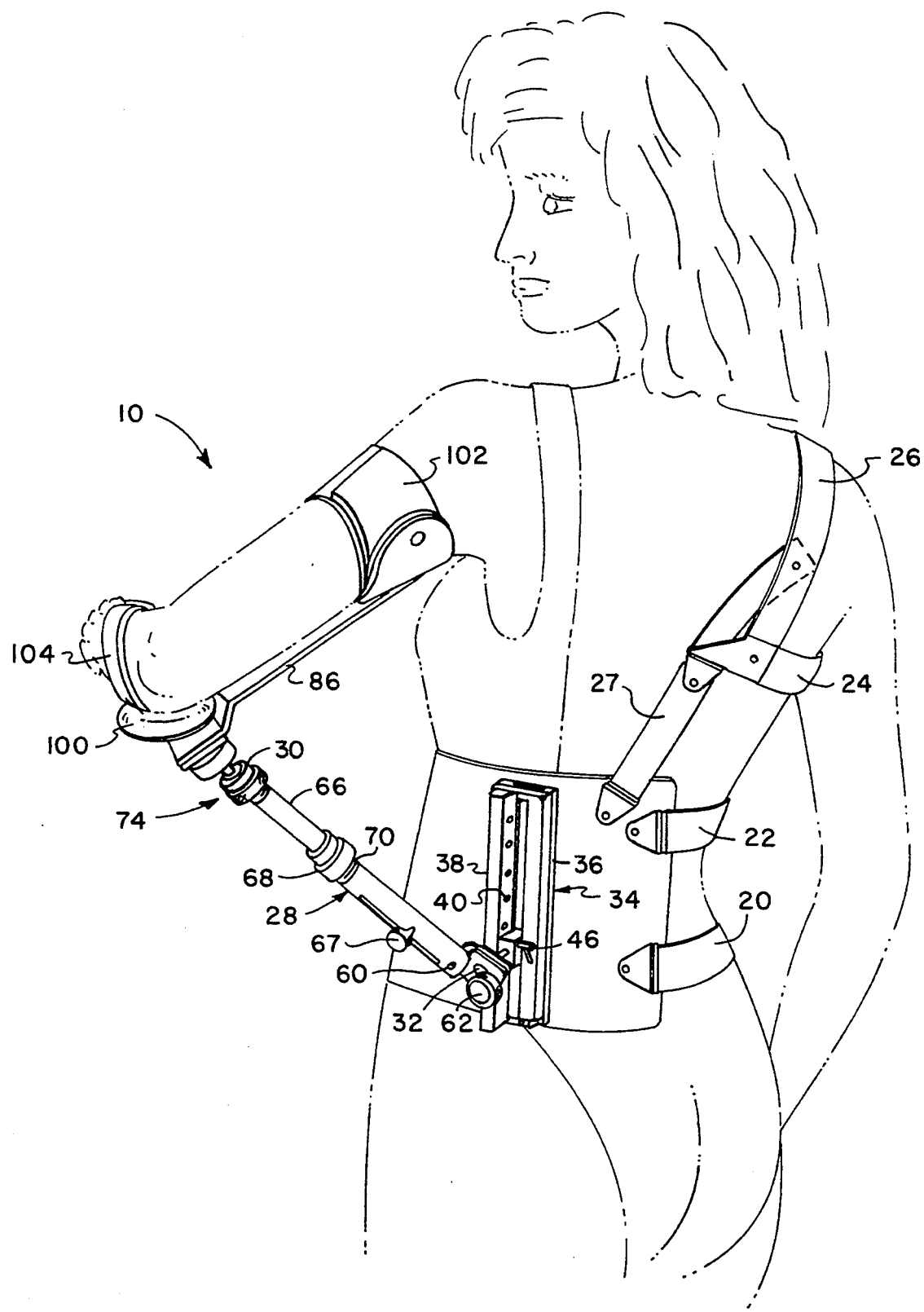
FIG. 2 is a rear perspective view of the orthopedic brace shown in FIG. 1.

Referring to FIGS. 1 and 2, the orthopedic brace 10 of the present invention consists of a harness 12, an arm support assembly 14, and a positioning assembly 16. The harness 12 has a saddle 18 preferably made of a fairly stiff but not rigid sheet of material such as leather, neoprene, or polypropylene. The saddle 18 is curved so as to conform comfortably about the patient's waist. If desired, the saddle 18 may be padded on the side next to the patient. Connected to the front and back of the saddle 10 are belt straps 20, 22 which extend around the waist of the patient and attach the saddle 18 to the torso of the patient. Working in conjunction with belt straps 20, 22 to attach the saddle 18 to the torso are shoulder straps 24, 26 and a linking strap 27 which connect to the front and back of the saddle 18 and extend over the shoulder of the patient opposite the injured shoulder or injured arm. The belt straps 20, 22 could obviously be replaced by a single broad belt, and the saddle 18 could be constructed as a continuous broad belt, without departing from the spirit of the invention. Similarly, the shoulder straps 24, 26 shown reversible in this embodiment, could be constructed symmetrically front and rear without departing from the spirit of the invention.

Referring again to FIGS. 1 and 2, the positioning assembly 16 includes a positioning rod 28, an upper universal joint 30, a lower universal joint 32, and an adjustable mounting assembly 34. The adjustable mounting assembly 34 includes a mounting rack 36 which is mounted substantially vertically to the saddle 18. As seen best in FIGS. 3 and 5, the mounting rack 36 has a shoulder 38 extending outwardly therefrom and running longitudinally along mounting rack 36. Location index holes 40 are drilled through the shoulder 38 with their axes parallel to the surface of the mounting rack 36 which faces away from the saddle 18. Also running longitudinally along the mounting rack 36 is a channel 42, which has a T-shaped cross-section. A mounting block 44, which also has a T-shaped cross-section, is slidably received in the channel 42. The mounting block 44 can slide vertically in channel 42 to a variety of vertical locations corresponding to the location holes 40. A location pin 46 extends horizontally through the mounting block 44 and into a selected one of the location index holes 40. The location pin 46 can be locked into place in the mounting block 44 for example by a cam coupling which expands against the diameter of the location pin 46, or by being threaded into the mounting block 44.

Figure 3:
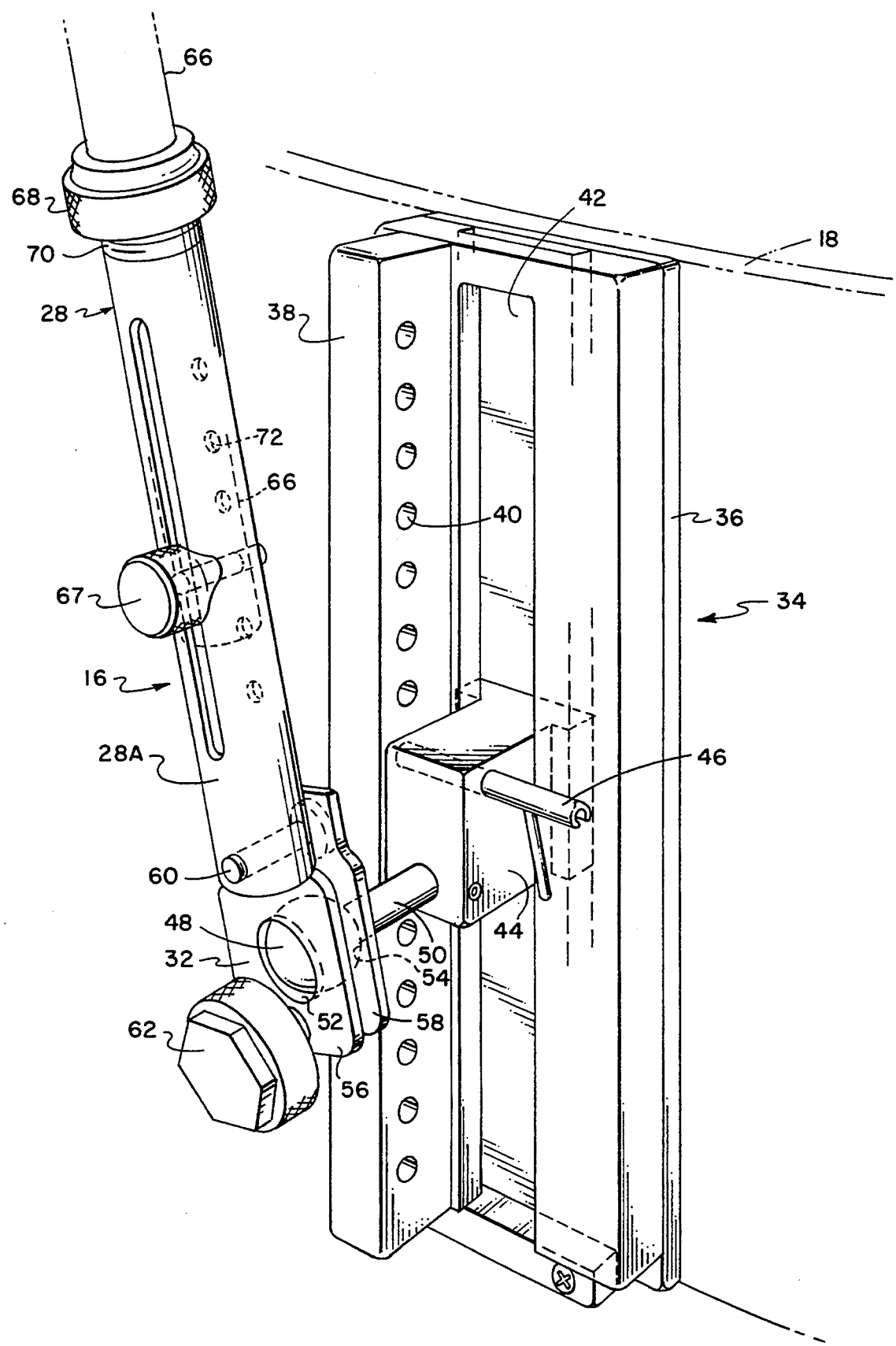
FIG. 3 is a perspective view of the lower end of the positioning assembly of the present invention.
Figure 5:
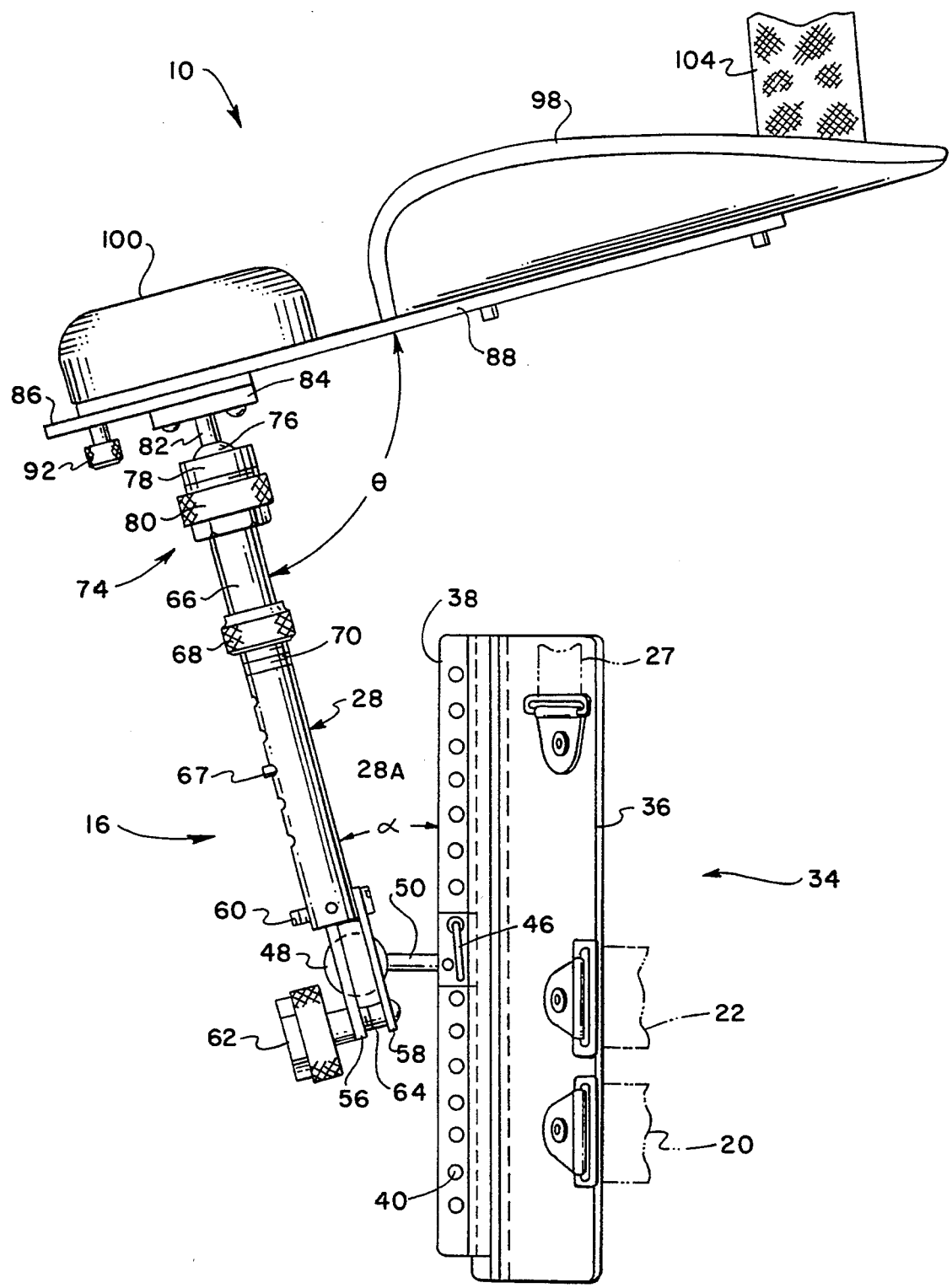

As seen in FIGS. 1 and 2, the lower universal joint 32 is rigidly mounted to the adjustable mounting assembly 34. Specifically, as shown in FIGS. 3 and 5, a lower ball 48 is coupled to the mounting block 36 by an arm 50. The lower ball 48 is in turn received in circular apertures 52, 54 and is rigidly captured between socket plates 56, 58, which grip the lower ball 48 in circular line contact. The socket plates 56, 58 are attached to the positioning rod 28 by mounting screw 60. The force with which the socket plates 56, 58 grip the lower ball 48 is determined by adjustment of an adjustment nut 62 which is threaded onto an adjustment screw 64.

Still referring to FIGS. 3 and 5, the positioning rod 28 extends upwardly from the lower universal joint 32. Specifically, the positioning rod 28 has a barrel 28A attached at its lower end to the socket plates 56, 58 and has a telescoping inner rod 66 extending through its upper end. The inner rod 66 may be positioned at any selected longitudinal position along the positioning rod 28 and is held rigidly in place by tightening a clamp nut 68 onto the positioning rod 28 and thereby squeezing a threaded collet 70 onto the inner rod 66. An index location pin 67 is retractably inserted transversely through a hole 72 formed in the inner rod 66. If the selected longitudinal position of inner rod 66 relative to the barrel 28A causes the index pin 67 to align with one of index holes 72, the index pin 67 will penetrate the aligned index hole 72 and thereby assist in maintaining the relative longitudinal positions of inner rod 66 and the barrel 28A.

Figure 4:
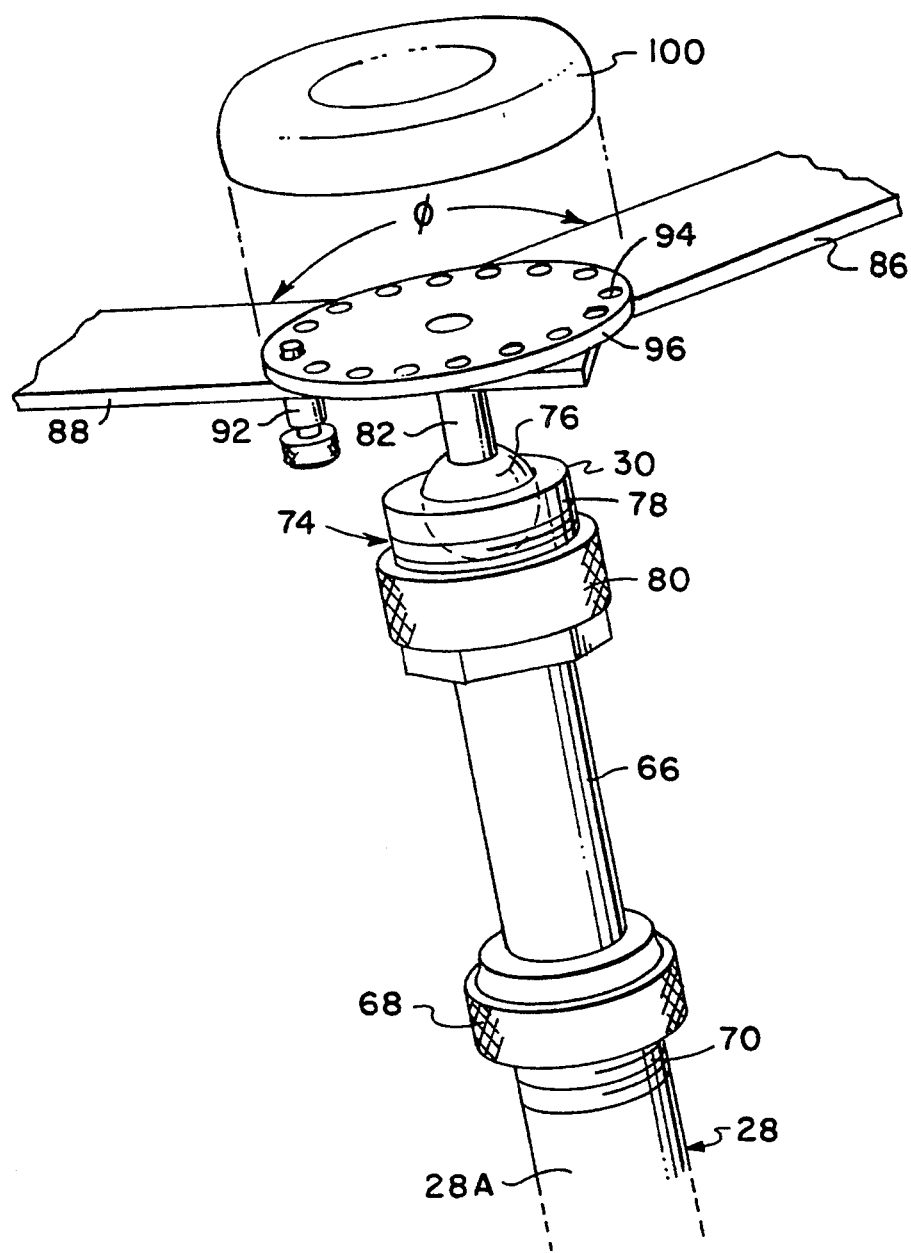
FIG. 4 is a perspective view of the upper end of the positioning assembly of the present invention; and, FIG. 5 is a front elevational view of the positioning assembly and forearm support of the present invention, configured as intended to be worn on the right arm of a patient.

Referring now to FIG. 4, the inner rod 66 is attached at its upper end to an upper universal joint 74. The upper universal joint 74 includes an upper ball 76 captured between an inner socket housing 78 and an outer socket housing 80, which rigidly grip upper ball 76 in circular line contacts. Such contact is achieved in this socket by circular shoulders formed in the socket housings 78, 80. The upper universal joint 74 is similar to the joint disclosed in U.S. Pat. No. 4,708,510. The gripping force applied to the upper ball 76 is determined by tightening the outer socket housing 80 onto the threads of inner socket housing 78. Both the type of ball and socket joint shown as upper universal joint 74 and the type shown as lower universal joint 32 may be used interchangeably as desired, with minor modifications. As seen in FIG. 5, an arm 82 extends from the upper ball 76 and is rigidly attached to an end plate 84.

Referring again to FIGS. 1 and 2, the arm support 14 includes generally an upper arm support bar 86 and a forearm support bar 88, which are adjustably attached together at a selected angle which corresponds to the desired angle of the patient's elbow. The upper universal joint end plate 84 is attached to the upper end of the forearm support bar 88, which is in turn attached to the lower end of upper arm support bar 86 by a screw (not shown) threaded into the upper end of upper ball arm 82. As shown in FIG. 4, the relative angular orientation $\phi$ of the support bars 86, 88 is determined by the insertion of an elbow angle set pin 92 into one of multiple adjustment holes 94. The elbow angle adjustment holes 94 are arranged in a circular pattern around the periphery of an elbow angle coupling plate 96 to provide a full range of the elbow angular adjustment. The set pin 92 may be threaded into one of the support bars 86, 88 or it may be a spring loaded pin permanently retained in a slip pocket formed in the support bar 88.

The elbow angle coupling plate 96 is attached to the lower end of the upper arm support bar 86. As shown in FIG. 5, the upper arm support bar 86 may be rotated relative to the forearm support bar 88 sufficiently to configure the apparatus for supporting the patient's left or right arm. A forearm splint or contour pad 98 and elbow pad 100 are attached to the upper surface of the forearm support bar 88 by suitable means, for example by adhesive or riveting. Also attached in a conventional way are an upper arm strap 102 and a forearm strap 104 to secure the patient's arm to the upper arm support bar 86 and the forearm contour pad 98, respectively.

The orthopedic brace 10 of the present invention will now be illustrated by a brief description of its manner of use. The harness 12 is placed on the patient's torso, with the shoulder straps 24, 26 wrapped about the uninjured shoulder. The patient's arm is secured to the arm support 14 by the arm straps 102, 104. The elbow angle $\phi$ is set as desired by retracting the set pin 92, spreading the support bars 86, 88 to the desired angle, and inserting the set pin 92 into selected adjustment hole 94. The mounting block 44 is positioned at the desired height as a rough adjustment of arm elevation, and the location pin 46 is inserted into the selected location index hole 40. Fine adjustment of arm elevation is made by loosening the clamp nut 68, retracting the location pin 46, sliding the inner rod 66 longitudinally to the selected position, and tightening the clamp nut 68. Upon alignment of the inner rod 66, the location pin 46 may be inserted in the appropriate index hole 40.

The upper arm and forearm orientations are set as desired, with the orientation angles $\alpha$, $\delta$ and $\theta$ being adjusted and set by adjusting the upper universal coupling joint 30 and the lower universal coupling joint 32, and thereafter tightening the adjustment nut 62 and the clamp nut 68.

The preferred embodiment has been described in order to illustrate the elements of the present invention. Modifications to the disclosed embodiment which do not depart from the invention will be appreciated by persons skilled in the art. Such modifications are intended to be encompassed within the following claims.

What is claimed is:

1. An orthopedic brace for supporting a person's forearm, elbow and upper arm, comprising:
   means for attaching the brace securely to a person's torso;
   means coupled to the attaching means for immobilizing and supporting a person's forearm, elbow and upper arm relative to the person's shoulder;
   means for selectively positioning and locking said supporting means at a desired elevation and at a desired orientation relative to the attaching means;
   the immobilizing means including means for selectively positioning and locking the person's forearm, elbow and upper arm at a desired elbow angle; and,
   wherein the elevation of the supporting means can be varied by selectively varying a location at which the positioning means mounts to the supporting means.

2. The orthopedic brace defined in claim 1, wherein the elevation of the supporting means can be varied by selectively varying a longitudinal dimension of the positioning means.

3. The orthopedic brace defined in claim 1 or claim 2, wherein the elevation of the supporting means can be varied by selectively varying an elevation at which the positioning means mounts to the attaching means.

4. The orthopedic brace defined in claim 1, wherein the positioning means is adjustably coupled to the torso attachment means at a first orientation angle; and,
   the orientation of the supporting means can be varied by selectively varying the first orientation angle.

5. The orthopedic brace defined in claim 1, wherein the positioning means is adjustably coupled to the supporting means at a second orientation angle; and,
   the orientation of the supporting means can be varied by selectively varying the second orientation angle.

6. An orthopedic brace for the human arm and shoulder, comprising:
   a harness configured to firmly attach said brace to a human torso;
   a mounting rack affixed to said harness;
   a mounting block configured to selectively attach at a plurality of locations arranged substantially vertically along said mounting rack;
   a first universal joint coupled to said mounting block;
   a positioning rod of selectively variable length having a first end portion coupled to the first universal joint at a first selected orientation angle and having a second end portions;
   a second universal joint coupled to the second end portion of said positioning rod at a second selected orientation angle;
   an arm support configured to firmly support a human arm flexed at a desired elbow angle, and coupled to said second universal joint; and,
   the positioning rod including first and second rod portions which are extendable and retractable in telescoping engagement with each other for varying the elevation of the arm support, and wherein the positioning rod has a plurality of mounting locations, selected by movement of the mounting block on the mounting rack, for varying the elevation of the arm support in relatively large increments.

* * * * *